United States Patent
Wiederkehr et al.

(10) Patent No.: US 11,179,181 B2
(45) Date of Patent: Nov. 23, 2021

(54) TROCHANTER PLATES

(71) Applicant: Stryker European Operations Holdings, LLC, Wilmington, DE (US)

(72) Inventors: Andreas Wiederkehr, Biel/Bienne (CH); Tim Lovell, Spokane, WA (US); Matthias Paulisch, Roggwil (CH); Pierre-Luc Sylvestre, Grenchen (CH); Erich Tschannen, Lommiswil (CH)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 145 days.

(21) Appl. No.: 16/441,771

(22) Filed: Jun. 14, 2019

(65) Prior Publication Data

US 2019/0380754 A1    Dec. 19, 2019

Related U.S. Application Data

(60) Provisional application No. 62/685,407, filed on Jun. 15, 2018.

(51) Int. Cl.
    *A61B 17/80*    (2006.01)
    *A61B 17/74*    (2006.01)
    (Continued)

(52) U.S. Cl.
    CPC .......... *A61B 17/8061* (2013.01); *A61B 17/74* (2013.01); *A61B 17/8057* (2013.01);
    (Continued)

(58) Field of Classification Search
    CPC . A61B 17/8061; A61B 17/74; A61B 17/8057; A61B 17/8085; A61B 17/8605;
    (Continued)

(56) References Cited

U.S. PATENT DOCUMENTS 3,284,995 A    11/1966  Haight
3,824,995 A    7/1974   Getscher et al.
(Continued)

FOREIGN PATENT DOCUMENTS

CN    102247204 A    11/2011
CN    102247205 B    8/2012
(Continued)

OTHER PUBLICATIONS

Biomet, Inc., "BMP Cable System Surgical Technique", Copyright 1998, pp. 1-16.
(Continued)

*Primary Examiner* — Marcela I. Shirsat
(74) *Attorney, Agent, or Firm* — Lerner, David, Littenberg, Krumholz & Mentlik, LLP

(57) ABSTRACT

A bone plate for implanting in a femur bone having a prosthesis implanted therein includes a shaft portion defining a plurality of holes and a trochanteric portion proximal to the shaft portion having two arms forming a concave shape and defining a plurality of first holes for receiving screws such that when implanted, the two arms at least partially wrap around and attach to the femur bone. The bone plate may include at least one bendable extension positioned between both of the arms. Each of the extensions may define at least one second hole.

19 Claims, 4 Drawing Sheets

(51) Int. Cl.
*A61B 17/86* (2006.01)
*A61F 2/32* (2006.01)

(52) U.S. Cl.
CPC ........ *A61B 17/8605* (2013.01); *A61B 17/746* (2013.01); *A61B 17/8085* (2013.01); *A61B 17/8625* (2013.01); *A61F 2/32* (2013.01)

(58) Field of Classification Search
CPC . A61B 17/809; A61B 17/8625; A61B 17/746; A61B 2017/564; A61F 2/32
USPC ....... 606/291, 280, 283, 284, 285, 286, 297, 606/324, 330, 86 R, 89, 902; 623/22.12
See application file for complete search history.

(56) References Cited

U.S. PATENT DOCUMENTS

| | | | |
|---|---|---|---|
| 5,015,248 A | 5/1991 | Burstein et al. | |
| 5,607,430 A | 3/1997 | Bailey | |
| 5,665,088 A | 9/1997 | Gil et al. | |
| 6,045,909 A | 4/2000 | Wang et al. | |
| 6,338,734 B1 | 1/2002 | Burke et al. | |
| 6,589,246 B1 | 7/2003 | Hack et al. | |
| 7,207,090 B2 | 4/2007 | Mattchen | |
| 7,229,444 B2 | 6/2007 | Boyd | |
| 7,635,365 B2 | 12/2009 | Ellis et al. | |
| 8,147,493 B2* | 4/2012 | Dutoit | A61B 17/8085 606/65 |
| 8,267,972 B1 | 9/2012 | Gehlert | |
| 8,469,967 B2 | 6/2013 | Pratt et al. | |
| 8,764,809 B2 | 7/2014 | Lorenz et al. | |
| 8,906,072 B2 | 12/2014 | Norris et al. | |
| 9,138,267 B2 | 9/2015 | Cavallazzi | |
| 9,339,313 B1 | 5/2016 | Powlan | |
| 9,681,902 B2 | 6/2017 | Christen | |
| 10,213,237 B2 | 2/2019 | Wiederkehr | |
| 2004/0210220 A1* | 10/2004 | Tornier | A61B 17/8061 606/284 |
| 2005/0273983 A1 | 12/2005 | Mattchen | |
| 2006/0217722 A1 | 9/2006 | Dutoit et al. | |
| 2008/0086137 A1* | 4/2008 | Probe | A61B 17/748 606/246 |
| 2008/0234679 A1 | 9/2008 | Sarin et al. | |
| 2009/0312758 A1 | 12/2009 | Petit et al. | |
| 2010/0234896 A1 | 9/2010 | Lorenz et al. | |
| 2015/0182266 A1 | 7/2015 | Jakob et al. | |

FOREIGN PATENT DOCUMENTS

| | | |
|---|---|---|
| CN | 202723964 U | 2/2013 |
| CN | 103610494 A | 3/2014 |
| CN | 104146757 A | 11/2014 |
| CN | 104188717 A | 12/2014 |
| CN | 104224300 A | 12/2014 |
| CN | 104352270 A | 2/2015 |
| EP | 0347874 B1 | 12/1989 |
| EP | 0615728 A2 | 9/1994 |
| EP | 1389940 A2 | 2/2004 |
| EP | 1781961 A2 | 5/2007 |
| EP | 2117452 B1 | 11/2009 |
| EP | 2432401 A1 | 3/2012 |
| EP | 3043729 B1 | 8/2017 |
| JP | 4829236 B2 | 12/2011 |
| RU | 2564967 C1 | 10/2015 |

OTHER PUBLICATIONS

DePuy Synthes, "Trochanter Stabilization Plate for DHS Implants: Extends DHS PLate Construct to Help Stabilize Greater Trochanter", Copyright 2000-2017, pp. 1-15.

Kinamed, Inc., "SuperCable Grip and Plate System", Copyright 2015, pp. 1-20.

Stryker, "Dall-Miles Recon and Trauma Cable System: Surgical Protocol", Copyright 2010, pp. 1-10.

Zimmer, Inc., "Cable-Ready Greater Trochanteric Reattachment: Surgical Technique", Copyright 2010, pp. 1-12.

Extended European Search Report including the Written Opinion for Application No. EP 19180024.2 dated Nov. 4, 2019, 9 pages.

* cited by examiner

TROCHANTER PLATES

CROSS-REFERENCE TO RELATED APPLICATIONS

This application claims the benefit of the filing date of U.S. Provisional Patent Application No. 62/685,407, filed on Jun. 15, 2018, the disclosure of which is hereby incorporated by reference herein.

BACKGROUND OF THE INVENTION

The present disclosure generally relates to bone plates, and in particular, to plates for the trochanteric region of a femur bone.

Bone plates for fracture treatment have to be firmly fixed to the bone to prevent bone fragments from moving relative to each other. When fixing a bone plate to bone, particular care has to be taken in case of periprosthetic fractures, which occur around an already implanted joint prosthesis.

Periprosthetic fractures typically occur around a joint prosthesis partially extending into a medullary canal of a fractured bone, such as a proximal femur prosthetic device (e.g., with a ball joint and a stem). When the fracture is to be treated, the surgeon generally has to keep in mind that the fixation elements must not intrude into the prosthetic device that has been implanted. This is especially difficult in the trochanteric region of the femur and there exists a need for an improved plate for use in fixing such fractures.

BRIEF SUMMARY OF THE INVENTION

The present disclosure includes different aspects of bone plates configured to hold fracture parts of a femur together to promote healing of the fractured bone.

A first aspect of the present disclosure is a bone plate for implanting in a femur bone having a prosthesis implanted therein, the plate includes a shaft portion defining a plurality of holes and a trochanteric portion proximal to the shaft portion. The trochanteric portion includes two arms forming a concave shape and defines a plurality of holes for receiving screws, such that when implanted, the two arms at least partially wrap around and attach to the femur bone.

In other embodiments, at least some of the plurality of holes of the arms may have trajectories such that screws implanted within the holes do not collide with the prosthesis. The arms may form a substantially "U" shape. The arms may wrap around and attach to opposite surfaces of the femur bone. The opposite surfaces may be the anterior and posterior surfaces of the femur bone. At least some of the holes of the arms may be configured for polyaxial locking of screws. The arms may define an open interior region for muscle and soft tissue attachment. When the bone plate is implanted on the femur bone, the open interior region may be positioned on at least a portion of the greater trochanteric region of the femur bone. The arms may be curved radially inwardly. The shaft portion and the trochanteric portion may be integral. The shaft portion and the trochanteric portion may be separate pieces attached to each other. In such an arrangement, the trochanteric portion may include a central portion, and each arm may be positioned on an opposing side of the central portion. The shaft portion and the trochanteric portion may be attached by a screw. The holes of the arms may be configured to receive locking and non-locking screws. The plate may include at least one bendable extension positioned between the two arms. In some examples, the plate may include two bendable extensions positioned between the two arms. Each bendable extension may define a hole for receiving a screw.

A second aspect of the present disclosure is a bone plating system for implanting in a femur bone having an already implanted prosthesis therein, the bone plating system includes a bone plate, a first and a second screw. The bone plate has a shaft portion that defines a plurality of holes and a trochanteric portion proximal to the shaft portion. The trochanteric portion has two arms that form a concave shape. The two arms define a plurality of first holes for receiving screws. The trochanteric portion also has at least one and may have two bendable extensions positioned between both of the arms, and each extension defines at least one second hole. The first screw includes a shaft that has a first length, and the second screw has a shaft that has a second length, the second length being less than the first length. When implanted in the femur, the first screws are implanted within the first holes of the arms and the second screws are implanted within the second holes of the extensions.

In other embodiments, the shaft portion and the trochanteric portion of the bone plate may be integral. The shaft portion and the trochanteric portion of the bone plate may be separate pieces attached to each other. The arms may form a concave shape which defines an open interior region. The arms may define a U-shape. The arms may at least partially wrap around and attach to the femur bone. The arms may attach to opposite surfaces of the femur bone. The opposite surfaces may be the anterior and posterior surfaces of the femur bone.

Another aspect of the present disclosure is a method of implanting a bone to a femur bone, the femur bone having an already implanted prosthesis within a medullary canal of the bone. The method includes attaching a shaft portion of the bone plate to the bone along a longitudinal axis of the bone by inserting a plurality of screws into a plurality of screw holes extending through the shaft portion, and attaching two arms of a trochanteric portion of the bone plate to the femur bone such that the two arms at least partially wrap around and attach to the femur bone.

In other embodiments, the two arms may wrap around and attach to opposite surfaces of the femur bone. The arms may wrap around and attach to anterior and posterior surfaces of the femur bone. The arms together may have a concave shape that may be substantially U-shape defining an interior region, the interior region is positioned on at least a portion of the greater trochanteric region of the femur bone. The step of attaching the arms may include inserting a first screw through a first hole of a first arm. The first screw may be implanted through the first hole of the first arm and may extend through the bone and terminates adjacent to or in contact with a second hole of the second arm. The method may include the step of attaching at least one bendable extension to the femur bone. The method may include the step of attaching two bendable extensions to the femur. The method may include the step of attaching two bendable extensions to the femur bone by implanting two second screws through respective holes of the extensions, the second screws having a shaft shorter than a shaft of the first screw. The method may include inserting a third screw through one of the plurality of holes of the shaft portion and into the lesser trochanteric region of the femur bone. The method may include attaching the trochanteric portion of the bone plate to the shaft portion of the bone plate after the shaft portion has been attached to the bone but before the trochanteric portion has been attached to the bone.

DETAILED DESCRIPTION

Figure 1:
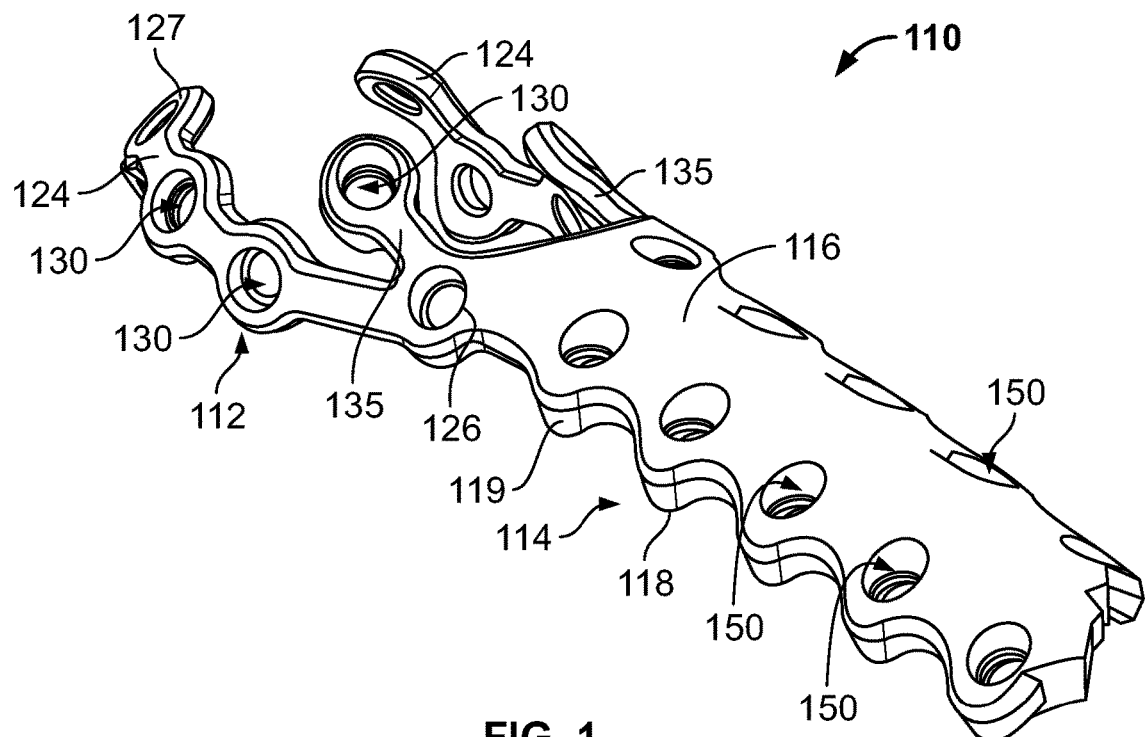
FIG. 1 is a perspective side view of a bone plate according to a first embodiment of the present disclosure.

As used herein, the term "proximal" refers to a location closer to an individual's heart, and the term "distal" refers to a location farther away from the individual's heart. When used in the context of an implant, the terms "proximal" and "distal" refer to locations on the implant closer to, or farther away from, the heart when the implant is implanted in an intended manner. The term "anterior" means toward the front part of the body, and the term "posterior" means toward the back of the body.

The present disclosure includes various embodiments of bone plates configured to hold fracture parts of a bone, such as a femur, together to promote healing of the fractured bone. Throughout the description, the same reference numerals are used to refer to identical or substantially similar elements in different embodiments, but within different 100-series of numbers (e.g., 100, 200, 300, etc).

FIGS. 1-4 show bone plating system 100 according to a first aspect of the present disclosure. System 100 includes trochanter plate 110 and a plurality of screws including tunnel screws 160, elongated screws 159, and sinkhole screws 170.

Plate 110 includes a trochanter portion 112 at a proximal end of the plate and a shaft portion 114 positioned distally of the trochanter portion. Shaft portion 114 may be anatomically preformed to form a curved shape for proper fit with a bone of a patient, and may be formed to conform to a femur bone. In certain embodiments, however, the plate may be bendable or otherwise capable of being formed to fit the bone. Plate 110 includes upper surface 116, lower surface 118 opposite the upper surface, and side walls 119 extending between the upper and lower surfaces. When plate 110 is implanted in bone, upper surface 116 is directed away from the bone to be treated and lower surface 118 is directed toward the bone. In the illustrated embodiment, side walls 119 have a wave-shaped profile.

Shaft portion 114 includes a plurality of screw holes 150 extending through upper and lower surfaces 116, 118. Screw holes 150 are configured to receive a screw for insertion into bone. In the illustrated embodiment, screw holes 150 are positioned in a spaced apart relationship along the sides of the shaft portion.

Some or all of the screw holes 150 are shaped to accommodate both locking and non-locking screws and may include a polyaxial locking feature within the inner circumference of the hole to allow such screws to be arranged in the hole in polyaxial orientations. For example, the holes may be adapted to allow a screw to move within a cone of between about 15 and 45 degrees cone, and preferably about a cone of 30 degrees. It is contemplated that the locking features of the holes may be any type of design, including, but not limited to, threaded holes or holes including SMARTLock® technology as offered by Stryker Corporation.

Figure 2:
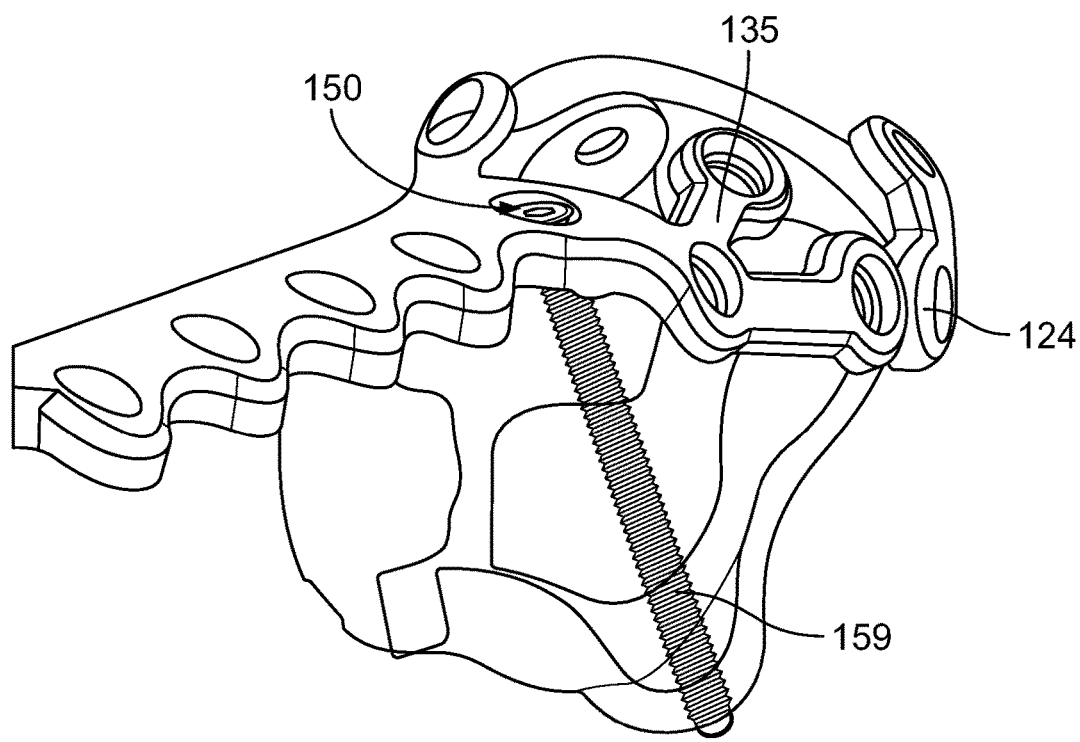
FIG. 2 is a schematic view of the bone plate of FIG. 1 shown on the proximal end of a femur including the trochanteric region of the femur bone.
Figure 3:
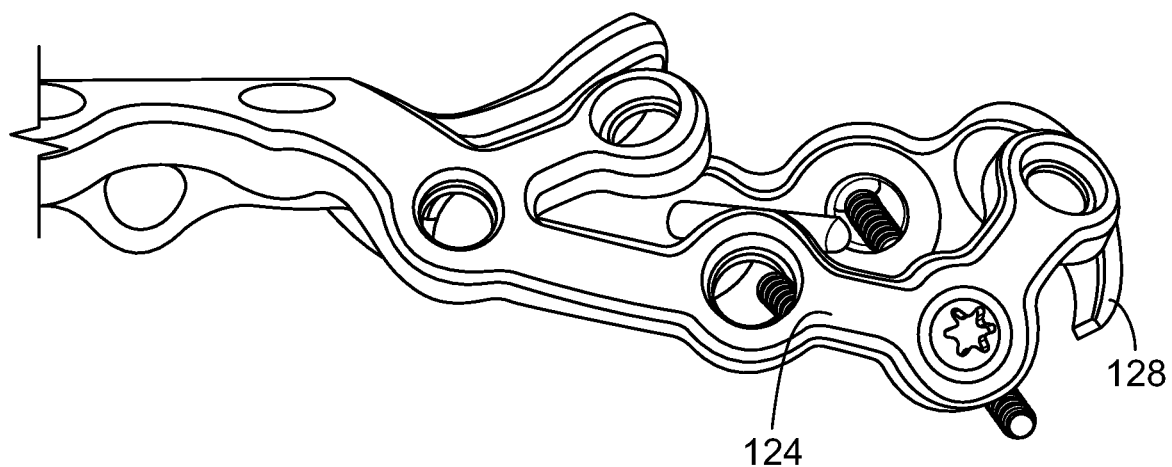
FIG. 3 is a side view of a proximal portion of the bone plate of FIG. 1.

As shown in FIG. 2, at least one of the screw holes 150 is designed to receive an elongated screw 159 having an elongated shaft for fixation within the lesser trochanter, in the case of the fractured bone being a femur bone. The elongated shaft of screw 159 fixes the plate to the denser bone of the lesser trochanter to help facilitate fixation.

Trochanter portion 112 includes two arms 124 extending generally proximally to shaft portion 114. Arms 124 extend from a first end 126 to a free second end 127. The two arms 124 define a concave shape which may be a substantially U-shaped configuration of the trochanteric portion 112 to define an open region 136, best shown in FIG. 4. Arms 124 are curved and extend radially inwardly toward a central axis of the plate 110 at second end 127, shown from the top view of FIG. 4. Additionally, the curved nature of the arms can also be seen from the side view shown in FIG. 3. As such, the arms form a hook or claw shape, which allows arms 124 to conform to (i.e., to wrap around) the bone. Additionally, each arm 124 may include a hook 128 at second end 127 to aid in fixation of the plate into the bone, in particular the hook may aid in the initial fixation of the plate.

Each arm 124 includes a plurality of screw holes 130 for receiving a screw. For example, tunnel screws 160 and/or sinkhole screws 170, each described below, or any other type of screw may be received within the screw holes 130. In the preferred embodiment, each arm includes four screw holes 130 spaced apart along a length of the arm between first end 126 and second end 127. The plurality of screw holes 130 on the arms 124 are each configured to receive both locking and non-locking screws.

Figure 4:
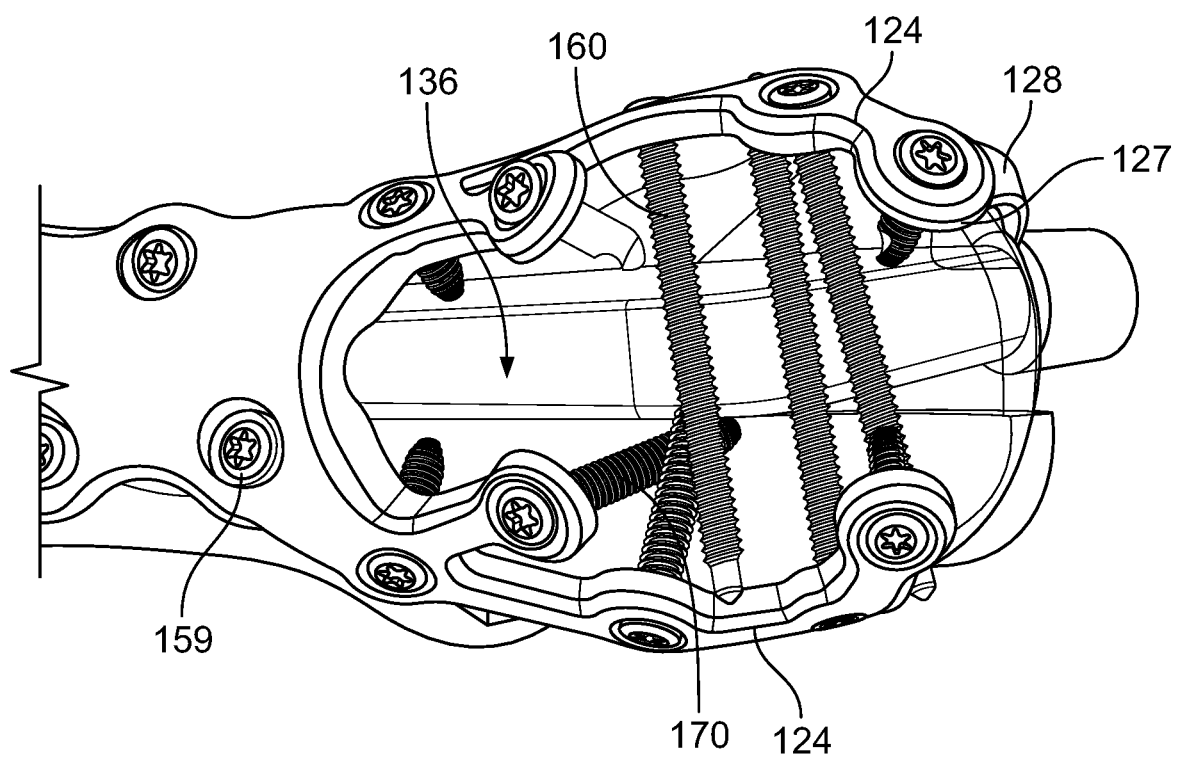
FIG. 4 is a top view of the bone plate of FIG. 1 implanted on a femur with an already implanted prosthesis therein.

With reference to FIG. 4, tunnel screws 160 may be inserted in a first screw hole 130 of a first arm and pass across the interior region 136 to catch or come in close proximity to an opposite hole of the second arm. Screw holes 130 are positioned on arms 124 in such a manner that allows the tunnel screws 160 to extend from one arm to the other without interference from the already implanted prosthesis, such as the stem of such prosthesis. Tunnel screws 160 extending across the bone in this manner allows for increased stability of the plate as the screws are able to catch more of the bone. In addition to the tunnel screws, sinkhole screws 170 having shorter shafts than tunnel screws 160 can be positioned within one or more of screw holes 130 for additional fixation. The shorter shaft of the sinkhole screws enable a shallower extension of the screw to prevent the screw from colliding with the implanted prosthesis. Additionally, preferably, sinkhole screws 170 are non-locking screws that create compression and facilitate fracture reduction. The design of the screws and the plate as a whole is such that there is minimal interference with an already implanted prosthesis.

Trochanter portion 112 also includes two extensions 135 extending in a generally proximal direction from the shaft positioned between the two arms 124. Extensions 135 are inclined and may be curved to conform to the bone. Extensions 135 are shorter in length than the arms 124 and include one screw hole 130 for receiving a sinkhole screw 170.

Arms 124 and extensions 135 are designed to exhibit some flexibility and bending to conform to the bone. The arms and extensions may be formed of the same material as the shaft 114, or the arms and extensions may be formed of a less stiff material to allow for increased flexibility. For example, the shaft may be formed of Titanium Grade 5 (Ti 6A1-4V) and the arms and/or extensions may be formed of a less stiff material, such as Titanium Grade 2. Alternatively or in addition to, the arms 124 and/or extension 135 may have a thinner thickness, measured from upper surface to lower surface, than the shaft 114 to allow for greater flexibility of the arms and/or extensions than the shaft, and in some examples the extensions may have a thinner thickness than the arms. It is also contemplated to include features such as necked-down regions that facilitate bending of the plate portions.

Some or all of the screw holes on the plate 110 may be formed from a softer material than the material that the plate is formed from to enable deformation of the hole for polyaxial locking of the screws, as is the case with the aforementioned SMARTLock® technology of Stryker.

When implanted on the bone, such as the proximal femur, the substantial U-shape of arms 124 is advantageous because this configuration allows for the tunnel screws 160 to have a trajectory extending from one side of the plate to the other without colliding with the implanted prosthesis. Additionally, the open interior region may defined by the arms may be positioned on a lateral surface of the femur bone and may be positioned on at least a portion of the greater trochanteric region of the femur bone. The interior region 136 may help to form an opening for soft tissue attachment which avoids the soft tissue to prevent irritation of the tissue. Additionally, when implanted on a femur bone, arms 124 may be positioned on the anterior-posterior regions of the bone. A first arm 124, anteriorly positioned, is placed on the bone so as to avoid the vastus lateralis and the gluteus minimus. A second arm 124, posteriorly positioned, is placed on the bone so as to avoid the gluteus medius attachment points. The posteriorly positioned arm Thus, the screws, at least for example tunnel screws 160, can be positioned in the anterior to posterior direction, which may protect the bursa and prevent soft tissue irritation thereby reducing patient pain.

Figure 5:
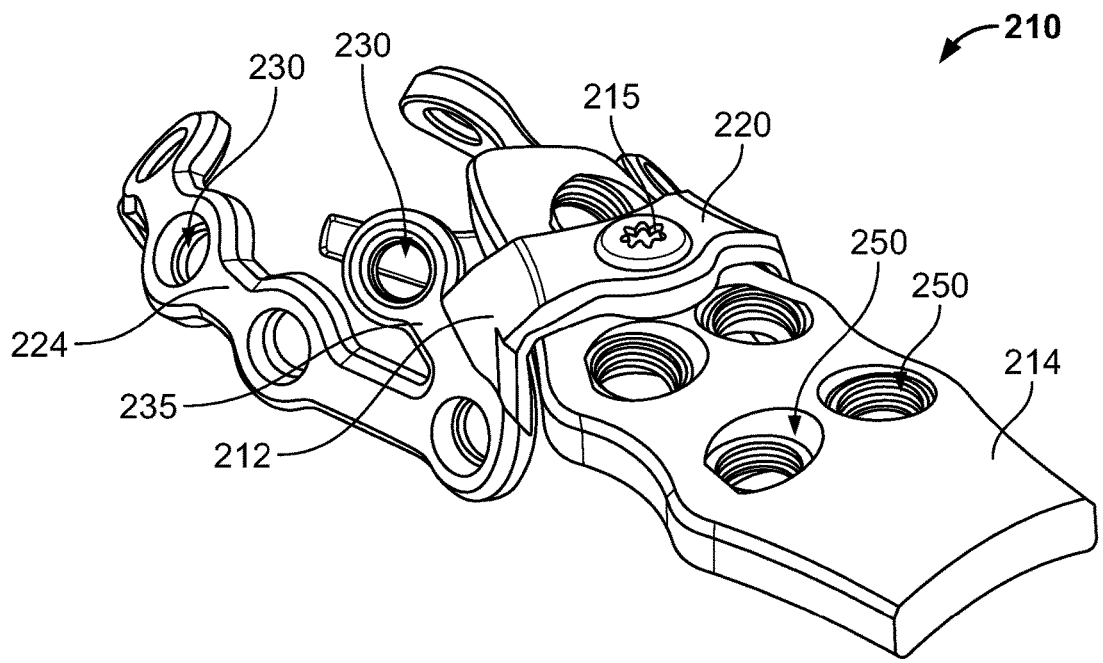
FIG. 5 is a perspective side view of a bone plate according to another embodiment of the present disclosure.
Figure 6:
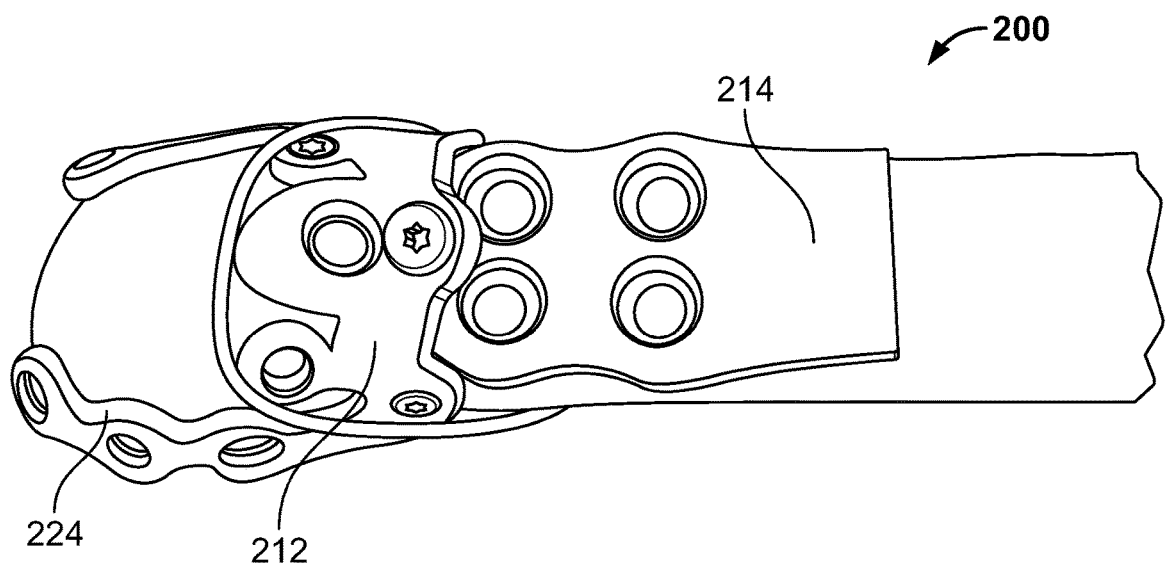
FIG. 6 is a photograph of a model of the plate of FIG. 5 shown on a model femur bone.

FIGS. 5 and 6 show bone plating system 200 including plate 210 according to another aspect of the present disclosure. System 200 and plate 210 is similar in many respects to system 100 and plate 110, the similar features of which will not be described again. However, while plate 110 is constructed as one single, integral piece having a shaft portion 114 and a trochanter portion 112, plate 210 includes a trochanter plate 212 and a fixation plate 214 that are two separate pieces connectable to one another to form the attached plate construct 210. In the illustrated embodiment, trochanter plate 212 is attached to the fixation plate 214 via connecting screw 215, although in other embodiments the plates may be connected by any method known in the art.

Generally, fixation plate 214 is designed for reduction of a fracture of a long bone, such as a femur, and can be used without the trochanter plate 212. Fixation plate 214 includes a shaft having a plurality of screw holes 250 for accommodating both locking and non-locking screws in polyaxial orientations. As described above with reference to screw holes 150, screw holes 250 include a polyaxial locking feature to allow the screws to be implanted at variable angles in bone. Additionally, fixation plate 214 may include one or more non-locking holes, and one such non-locking hole may be oblong.

Fixation plate 214 also includes a screw hole 250 located centrally along the width, measured from sidewall to sidewall of the plate, for receiving connecting screw 215 for attachment of the trochanter plate 212.

Trochanter plate 212 is similar in structure to trochanter portion 112 of plate 110. Trochanter plate 212 includes central portion 220 with a hole for receiving connecting screw 215 and two arms 224 and two extensions 235 disposed between the two arms. Arms 224 include a plurality of screw holes 230 designed to accommodate tunnel screws 160 and sinkhole screws 170, as well as other screws known in the art. Extensions 235 include one hole 230 for receiving a sinkhole screw. The placement and trajectories of the screws of plate 210 are substantially similar to that of plate 110 and arms and extensions exhibit similar flexing and bending capabilities, as described above.

Although the illustrated embodiment shows connecting screw 215 positioned centrally on the fixation plate 214 and central portion 220 of trochanter plate 212, in other examples, the connecting screw may be skewed or off-centered on one or both of the plates to allow the arms and extensions to sit in different positions on the bone.

FIG. 6 shows a photograph of system 200 positioned on a model femur bone. As shown, a guide wire may wrap around the proximal end of the system 200 and may extend on the upper surface of the arms 224. The trochanter plate 212 and/or the fixation plate 214 may include a notch for receiving the guide wire to ensure the proper and secure placement of the wire.

Figure 7:
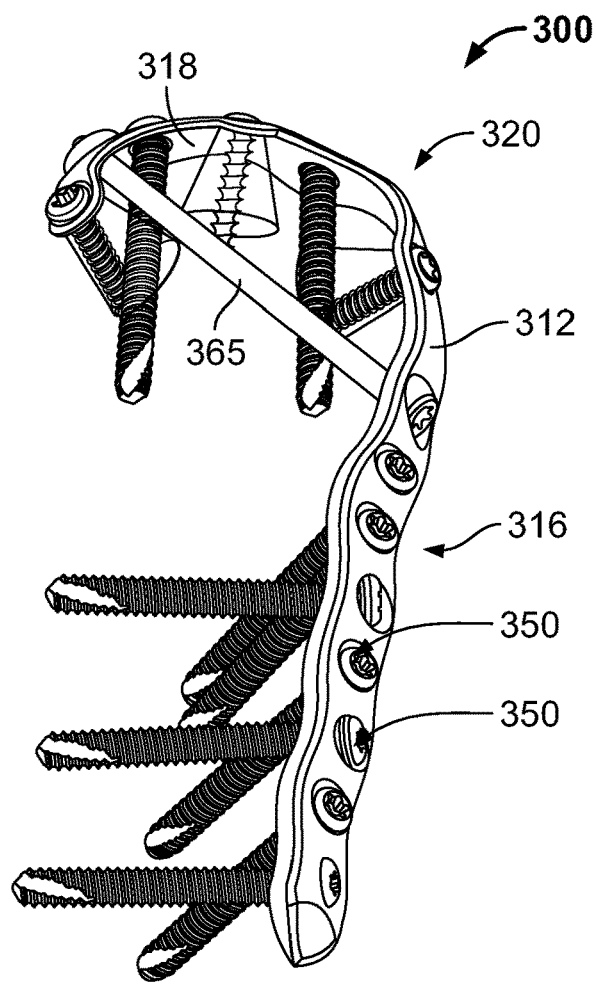
FIG. 7 is a perspective side view of a bone plating system according to another embodiment of the present disclosure.
Figure 8:
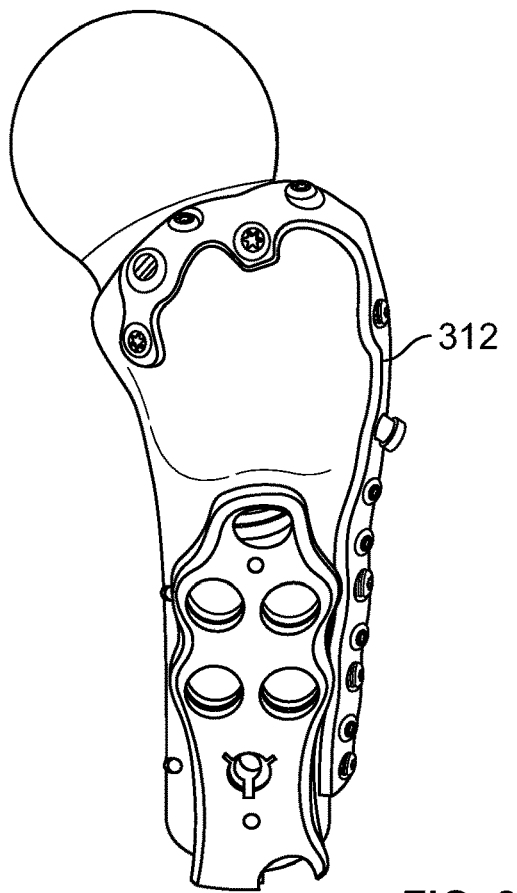
FIG. 8 is a schematic view of the bone plate of FIG. 7 implanted on a femur in conjunction with a fixation plate.

FIGS. 7 and 8 show bone plating system 300 according to another aspect of the present disclosure. System 300 includes trochanter plate 312 and elongated through-screw 365. In some examples, the system may include a fixation plate for fixing to the long bone, such as fixation plate 214 described above.

Trochanter plate 312 includes an elongated shaft 316 having a plurality of screw holes 350 capable of receiving both locking and non-locking screws in polyaxial orientations. Shaft 316 may include at least one oblong screw hole for receiving a non-locking screw. Trochanter plate 312 has a curved head portion 320 designed to wrap around the trochanteric region of the femur, as shown in FIG. 8. In position on the bone, the trochanter plate 312 may be shaped to form a substantially rounded "7" shape.

The head portion 320 includes holes 350 designed to accommodate screws having shafts of varying lengths. At least one through-screw 365 extends through two holes 350.

Head portion 320 may include spikes projecting from the lower surface 318 of the plate to aid in fixation of the plate to bone. Advantageously, the shape of the trochanter plate 312 allows for an open region on the bone for soft tissue and muscle attachment.

The present disclosure also includes various kits based on the components discussed above. While it is envisioned that these various components may be utilized, packaged, sold or designed in any number of systems and kits, representative embodiments will be described below.

The present disclosure can include a kit which can be packaged in a single package as a system or in multiple packages that can be selected as needed by the operator to form a system. For example, such a kit may include at least one plate 110, at least one tunnel screw 160, and at least one sinkhole screw 170. The kit may include an elongated screw 159. Any combination of components may be included in a single package or in separate packaging which are later brought together as a kit. If multiple components of any of the specific components are present, such components may differ in size, material, configuration, and the like, such that the operator can select a particular component from a variety of available components depending on need based on surrounding anatomy, bone size, bone density and the like.

Another kit envisioned by the present disclosure includes at least one trochanter plate 212 and at least one fixation plate 214. The kit may further include at least one tunnel screw, at least one sinkhole screw, and/or at least one elongated screw. The kit may be packaged in any combination of such components, and the components may be included in such kit in various sizes, configurations, and material to accommodate the needs of the patient.

The present disclosure also includes methods of use. A periprosthetic procedure for attaching bone plate 110 of system 100 to bone will be described.

First, the surgeon positions plate 110, particularly lower surface 118, on the fractured portion of the bone, such as a femur bone, such that the trochanteric portion 112 of the plate is positioned on at least a portion of the trochanteric region of the femur. The surgeon fixes the shaft portion 114 of the plate to the bone along the longitudinal axis of the bone. Due to the polyaxial locking capabilities of holes 150, the screws can be inserted at variable angles as needed. The surgeon can modify the placement of the arms 124 and extensions 135 to properly rest against the bone such that the arms wrap around at least a portion of the trochanteric region of the bone as shown in FIG. 4.

Next, at least one tunnel screw 160 is implanted within certain of the holes 130 of arm 124 and are implanted into the bone such that the tunnel screws extend through a first hole of a first arm and across the interior region 136 defined by the arms and catch or terminate adjacent a second hole 130 of the second arm. The tunnel screws 160 are implanted such that they do not interfere or collide with the already implanted prosthesis. The surgeon implants sinkhole screw 170 in at least one other hole 130 in the trochanteric portion 112 of the plate 110. The surgeon may implant a non-locking compression sinkhole screw 170 into at least one of the holes of the arms and/or into at least one of the holes of the extensions 135 such that the sinkhole screws 170 avoid the already implanted prosthesis. The surgeon may implant an elongated screw 159 through a hole 150 on the shaft portion and into the lesser trochanter region of the femur for increased stability. The various screws may be implanted in the bone in any order based on the needs of the specific circumstances.

A method of use of plate 210 is substantially similar to the method of use of plate 110, except that the surgeon first implants the fixation plate 114, at least provisionally, on the bone, and then the surgeon attaches the trochanteric plate 112 to the fixation plate. Thereafter, the plates are anchored to the bone as described above.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A bone plate for implanting in a femur bone having a prosthesis implanted therein, the bone plate comprising:
    a shaft portion defining a plurality of holes; and
    a trochanteric portion proximal to the shaft portion having two bendable extensions and two arms forming a concave shape and defining a plurality of holes for receiving screws, such that when implanted, the two arms are configured to at least partially wrap around and attach to the femur bone,
    wherein at least one of the holes in one arm is configured to direct an end of one of the plurality of screws to a position adjacent the other arm,
    wherein the two bendable extensions are positioned between the two arms such that the two arms extend further away from the shaft portion than the two bendable extensions.

2. The bone plate of claim 1, wherein at least some of the plurality of holes of the arms have trajectories such that screws implanted within the holes do not collide with the prosthesis.

3. The bone plate of claim 2, wherein the at least some of the plurality of the holes of the arms are configured for polyaxial locking of screws.

4. The bone plate of claim 1, wherein the arms define an open interior region.

5. The bone plate of claim 4, wherein when the bone plate is implanted, the open interior region is configured to be positioned on at least a portion of the greater trochanteric region of the femur bone.

6. The bone plate of claim 1, wherein the arms are curved radially inwardly.

7. The bone plate of claim 1, wherein the shaft portion and the trochanteric portion are integral.

8. The bone plate of claim 1, wherein the shaft portion and the trochanteric portion are separate pieces attached to each other.

9. The bone plate of claim 8, wherein the trochanteric portion includes a central portion, and each arm is positioned on an opposing side of the central portion.

10. The bone plate of claim 8, wherein the shaft portion and the trochanteric portion are attached by a screw.

11. The bone plate of claim 1, wherein the holes of the arms are configured to receive locking and non-locking screws.

12. The bone plate of claim 1, wherein each bendable extension defines a hole for receiving a screw.

13. A bone plating system for implanting in a femur bone having a prosthesis implanted therein, the bone plating system comprising:
    a bone plate having a shaft portion defining a plurality of holes and a trochanteric portion proximal to the shaft portion and having two bendable extensions with at least one second hole and two arms forming a concave shape and defining a plurality of first holes for receiving screws,
    wherein the two bendable extensions are positioned between the two arms such that the two arms extend further away from the shaft portion than the two bendable extensions;
    a first screw having a shaft having a first length; and
    a second screw having a shaft having a second length, the second length being less than the first length,
    wherein when implanted, the first screws are configured to be implanted within the first holes of the arms and the second screws are configured to be implanted within the second holes of the at least one extension, such that an end of the first screw is disposed adjacent the opposite arm within which it is implanted.

14. The bone plating system of claim 13, wherein the shaft portion and the trochanteric portion of the bone plate are integral.

15. The bone plating system of claim 13, wherein the shaft portion and the trochanteric portion of the bone plate are separate pieces attached to each other.

16. A method of implanting a bone plate to the femur bone, the femur bone having an already implanted prosthesis within a medullary canal of the bone, the method comprising:

attaching a shaft portion of the bone plate to the bone along a longitudinal axis of the bone by inserting a plurality of screws into a plurality of screw holes extending through the shaft portion;

attaching two arms and two bendable extensions of a trochanteric portion of the bone plate to the femur bone by inserting a plurality of screws through a second plurality of screw holes extending through the trochanteric portion such that the two arms at least partially wrap around and attach to the femur bone, wherein the two arms extend and attach further away from the shaft portion than the two bendable extensions.

17. The method of claim 16, wherein the step of attaching the arms includes inserting a first screw through a first hole of a first arm such that the first screw is implanted through the first hole of the first arm and extends through the bone and terminates adjacent to or in contact with a second hole of the second arm.

18. The method of claim 17, further comprising the step of attaching two bendable extensions to the femur bone by implanting two second screws through respective holes of the extensions, the second screws having a shaft shorter than a shaft of the first screw.

19. The method of claim 16, further comprising attaching the trochanteric portion of the bone plate to the shaft portion of the bone plate after the shaft portion has been attached to the bone but before the trochanteric portion has been attached to the bone.

* * * * *